United States Patent [19]
Griffith et al.

[11] Patent Number: 5,663,402
[45] Date of Patent: Sep. 2, 1997

[54] PROCESS FOR THE PREPARATION OF PHOSPHORODITHIOIC COMPOUNDS VIA THIONATION REACTION

[75] Inventors: Edward J. Griffith, Manchester; Toan M. Ngo, Eureka, both of Mo.

[73] Assignee: G.D. Searle & Company, Chicago, Ill.

[21] Appl. No.: 409,011

[22] Filed: Mar. 27, 1995

Related U.S. Application Data

[63] Continuation-in-part of Ser. No. 219,227, Mar. 29, 1994, Pat. No. 5,464,601.

[51] Int. Cl.$^6$ .................... C07F 9/17; C07F 9/205
[52] U.S. Cl. .................... 558/121; 423/303; 544/239; 544/240; 562/26
[58] Field of Search .................... 558/112, 121

[56] References Cited

U.S. PATENT DOCUMENTS

| | | | |
|---|---|---|---|
| 2,569,128 | 9/1951 | Jones | 23/206 |
| 2,794,705 | 6/1957 | Hudson | 23/206 |
| 3,524,725 | 8/1970 | Cremer et al. | 23/206 |
| 4,173,621 | 11/1979 | Krause et al. | 423/303 |
| 5,198,202 | 3/1993 | Engel et al. | 423/303 |

FOREIGN PATENT DOCUMENTS

| | | |
|---|---|---|
| 119198 | 4/1976 | Germany . |
| 297643 | 3/1971 | U.S.S.R. . |
| 306132 | 4/1971 | U.S.S.R. . |
| 10588775 | 7/1983 | U.S.S.R. . |
| 1301775 | 4/1987 | U.S.S.R. . |
| 3045 | 1/1903 | United Kingdom . |
| 14962 | 10/1915 | United Kingdom . |

OTHER PUBLICATIONS

R. A. Cherkasov et al, Organothiphosphorus Reagents in Organic Synthesis, *Tetrhedron Report Number 186*, vol. 41, No. 13, pp.2567–2624, 1985.

R. Bouloch, On the Mixtures Formed by Sulfur and Phosphorus at Temperatures above 100° C. Extract from the proceedings of the Jul. 21, 1902 meeting of the French Academy of Sciences, pp. 165–168. Translation from French.

V. V. Illiarionov et al, Investigation of Decomposition of Solid Solutions in the System Phosphorus–Sulfur, *Akademiya Nauk SSSR, Izvestiya Sektora FizikoKhimicheskogo Analiza*, vol. 21 (1953) pp. 153–158. Translation from Russian.

Phosphorus and its Compounds, Interscience Publishers, Inc., 1958.

V. V. Puchkarev and V.G. Berezyuk, "Study of the Reaction of $^{35}$S and $^{32}$P in Aqueous Alcohol Solutions with n–Tetradecylamine Hydrocholoride By the Foam Formation Method", translated from Radiokhimiya, vol. 10–, No. 4, pp. 433–438, Jul.–Aug., 1968.

Mazitova, F.N. and V.K. Khairullin. "New Method for the Synthesis of O,O–Diaryl Hydrogen Phosphorodithioates, O,O,O–triaryl Phosphorothioates, and Tetrakis(aryloxy) diphosphine Disulfides." *Journal of General Chemistry of the USSR* 50 (1980): 652–658.

Mazitova, F.N. and V.K. Khairullin. "Reactions of Aliphatic Alcohols with Sulfur and Red Phosphorus." *Journal of General Chemistry of the USSR* 50 (1980): 1393–1396.

*Primary Examiner*—Johann Richter
*Assistant Examiner*—Michael G. Ambrose
*Attorney, Agent, or Firm*—Fitzpatrick, Cella, Harper & Scinto

[57] ABSTRACT

There is disclosed a novel process for preparing products of the reaction of elemental phosphorus and elemental sulfur under reaction conditions wherein the phosphorus and sulfur are combined in a pre-mix at temperatures below the reaction temperature. The pre-mix may contain a diluent which is preferably the product of the reaction. Phosphorus pentasulfide can be prepared by heating the pre-mix to reaction temperatures wherein lower exotherm temperatures and reduced vibration are observed. Organophosphorus and thionated products can be prepared by the reaction of elemental sulfur and elemental phosphorus together with an organic compound wherein the ratio of phosphorus and sulfur generally corresponding to $P_2S_5$. The process obviates the need for separately preparing phosphorus pentasulfide to prepare thiohated and organophosphorus compounds.

9 Claims, 3 Drawing Sheets

PROCESS FOR THE PREPARATION OF PHOSPHORODITHIOIC COMPOUNDS VIA THIONATION REACTION

This application is a continuation-in-part of application Ser. No. 08/219,227 filed Mar. 29, 1994 now U.S. Pat. No. 5,464,601.

This invention relates to novel processes for the production of the sulfides of phosphorus by forming a liquid mixture of sulfur and phosphorus. Such feed material is maintained as a liquid and can be adjusted to provide an accurate, safe feed to the reactor for preparing such sulfides of phosphorus as phosphorus pentasulfide.

BACKGROUND OF THE INVENTION

The usual commercial method for preparing commercial quantities of phosphorus sulfides, particularly, phosphorus pentasulfide is to continuously introduce liquid phosphorus and liquid sulfur into a boiling mass consisting of phosphorus pentasulfide to effect a continuous reaction between the phosphorus and sulfur. The product may be removed from the reactor by continuous distillation of the reaction product. The control of the reaction is achieved by the rate of addition of the reactants and the proportions being added. Such a process is described in U.S. Pat. No. 2,794,705 to Hudson. While total reactant feed rate is mostly controlled by observing the temperature of the reaction, the control of proper proportions of each reactant being added can only be definitively provided by analysis of the product. Usually several hours are required to determine the result of readjusting feed rates, temperature, sojourn time and cooling rates based upon analytical work.

Because the reaction of phosphorus and sulfur is rapid and exothermic at the elevated temperatures commonly employed, many attempts have been made to render the reaction more controllable and efficient. In S.U. 1,301,775 the heat evolution from the reaction of phosphorus and sulfur is controlled by conducting the reaction at a temperature of 130° C. to 175° C. and providing a sulfur to phosphorus ratio of 3.5–4.0:1 until the temperature ceases to increase and then adding additional phosphorus to provide the desired stoichiometric amount, i.e., sulfur to phosphorus ratio of 5:2.

In another attempt to control the process to provide efficiency, there has been developed a continuous loop reactor containing a liquid reaction mixture which is continuously circulated. The liquid phosphorus and sulfur reactants are introduced into the loop so as to avoid a large concentration of phosphorus by feeding the phosphorus into the loop at a point in which there is a concentration of sulfur. The phosphorus sulfide product is removed from the reactor in the gaseous state. Such a process is described in U.S. Pat. No. 5,198,202 to Courant et al.

Due to the kinetics of the reaction between phosphorus and sulfur at such high temperatures as is normally encountered when removing product by distillation there is a vibration problem. One solution to this problem is to either use smaller reactors or to use a two stage reactor. In a first stage, usually a small reactor, phosphorus and sulfur are fed at a ratio to provide a phosphorus content of about 28%. In the second stage, the desired amount of phosphorus is added to provide the desired sulfide. While the in the first stage the reactor is operated at boiling point of the mixture, the second stage is operated at a temperature as low as 300°–353° C. Such a process is described in East German patent 119,198 to Strauss.

While the above noted prior art is directed to improved safety of the process further advances are needed to provide a truly efficient process which is also more safely and accurately operated.

SUMMARY OF THE INVENTION

There has been discovered an improved process for reacting phosphorus and sulfur in the molten state which enables efficient, safe and more accurately controlled reactions, said improvement comprising providing a feed material for such reaction which is a pre-mix comprising elemental phosphorus and elemental sulfur at relatively low temperatures and in predetermined ratios. Such mixtures of elemental phosphorus and elemental sulfur have been known but have never been utilized as feed material to a large, industrial process involving the reactions of phosphorus and sulfur in the molten state. An example of such a reaction is the process for preparing the sulfides of phosphorus, typically in a continuous process. When sulfur and phosphorus are mixed at relatively low temperatures below their reaction temperature, generally regarded as below about 120° C., a highly fluid liquid can be formed. This liquid is an atomic mixture of sulfur and phosphorus. Such mixtures are described in the report by V. V. Illariornov and T. I. Sokolova, in *Izvest. Fiz. Khim.* 21, pp. 153–158 (1952); by R. Bouloch in *Compt. rend.* pp. 165–168 (1902) and Van Wazer, "*Phsophorus and its Compounds*", Vol. 1, p. 289, Interscience, New York (1958).

DETAILED DESCRIPTION OF THE INVENTION

Figure 1:
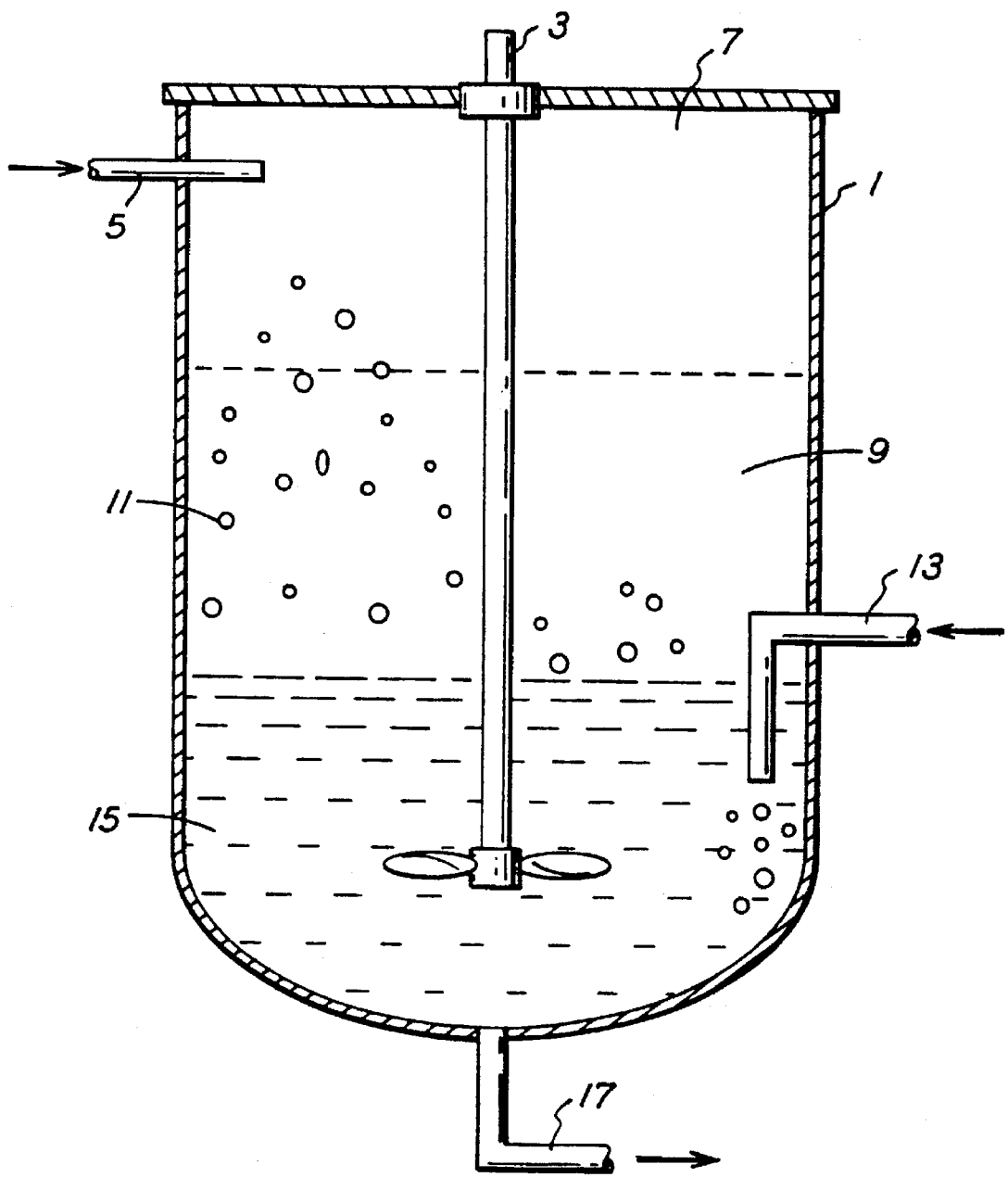
FIG. 1 is a schematic of one possible system for forming the liquid pre-mix material to be provided in a process for reacting sulfur and phosphorus.

In accordance with this invention there is provided an improved process for the production of the compounds resulting from the reaction of sulfur and phosphorus wherein the improvement comprises providing a pre-mix of elemental phosphorus and elemental sulfur at temperatures below the temperature of reaction of said elements. The most obvious advantage of the present invention is to allow the operator of the phosphorus sulfide reaction to prepare and quickly analyze by physical properties a pre-mixed feed mixture to the exact ratio desired in the finished phosphorus product. Analytical procedures are well known whereby the pre-mix can be analyzed and corrections made to bring the mixture into the desired range or exact ratio prior to entry into the reaction. Analytical methods which may be employed are index of refraction, viscosity and spectroscopy such as IR and visible spectroscopy. Exact ratios of phosphorus and sulfur will be dictated by the type of product desired, the most widely used such product being a sulfide and in particular phosphorus pentasulfide.

Another advantage of the process of this invention, particularly in the production of the sulfides of phosphorus, is the reduction in the amount of vibration occurring in the reactor since the introduction of pre-mixed phosphorus and sulfur will assure the operator that local concentrations of phosphorus will be less likely to occur. By pre-mixing the reactants there is ample opportunity for blending the ingredients of the pre-mix adequately before introduction into the reactor. A uniform mixture reduces the potential of reactant imbalance in the reactor thereby eliminating the root cause of most of the vibration commonly experienced in the reaction producing phosphorus pentasulfide.

The pre-mix of phosphorus and sulfur in accordance with this invention is generally held at a temperature of 100° C. or less and is typically held in the range of from about 30° C. to about 80° C. by typical means. The mixture may also be maintained under water as is known for white phosphorus. Since such temperature range is below the reaction temperature of these elements, approximately 120° C., the mixtures need only be protected from sources of heat. For safety however, the holding tank and transport lines are usually equipped with both heating and cooling means to control the temperature of the mixture.

The phosphorus typically employed in the process of this invention is white phosphorus. Typically phosphorus melts at 44.1° C. and is therefore easily blended with sulfur resulting in a mixture easily held in the liquid state. Elemental sulfur also exhibits several allottopic forms both in the liquid and solid phases. The crystalline rhombic form melts at 112° C. while the monoclinic form melts at 119° C. There are three liquid forms of sulfur known. The low temperature form, $S\lambda$, is presumed to be an eight membered ring. $S\pi$ and $S\mu$ are not well defined, but their existence is well established. $S\mu$, for example is not soluble in either carbon disulfide or liquid phosphorus. $S\mu$ is presumed to be long chains while $S\pi$ may be short chains. Equilibrium mixtures contain all three forms of the liquid sulfur. When elemental phosphorus and elemental sulfur are mixed at temperatures below 120° C. they do not react until initiated at higher temperature. Instead of reacting, they form alloys that are well behaved liquids at temperatures as low as 10° C., depending upon the ratio of phosphorus and sulfur content. The elements quickly dissolve in each other to form alloys, most of which are fluid, transparent, straw yellow liquids even at room temperature. At a phosphorus/sulfur ratio corresponding to phosphorus pentasulfide, the liquids crystalize to bright yellow crystals at temperatures less than 80° C. The phase diagram of these mixtures will be discussed below with relationship to the attached FIG. 2.

Typically, in a process for the production of a common sulfide such as $P_2S_5$, the proportion of the elements, by weight, is in the range of from about 72% to about 75% sulfur atoms and from about 25% to about 28% phosphorus atoms. Phosphorus pentasulfide is widely employed as an intermediate to prepare a wide range of different compounds such as insecticides, oil additives and rubber chemicals. Therefore one of the preferred pre-mixes of this invention will contain phosphorus and sulfur in a ratio which corresponds to such compound.

Also included in the pre-mix of this invention may be a minor portion of the diluent for the atomic mixture of phosphorus and sulfur. Preferably, such diluent is the phosphorus sulfide which is to be produced in the reaction between phosphorus and sulfur in the molten state. For example $P_2S_5$ can be employed as a diluent in the pre-mix of phosphorus and sulfur in the process for preparing phosphorus pentasulfide. Such diluent provides a dampening of the exotherm temperature which occurs when reaction temperature is reached. A minor portion means an amount up to less than 50%, by weight of the total mixture and is usually in the range of from about 2% to about 35% of the total mixture. Most typically, the amount of $P_2S_5$ diluent is in the range of from about 2% to about 10%, by weight of the total pre-mix. It has been found that the $P_2S_5$ diluent allows easy and rapid solution of the phosphorus and sulfur into a homogeneous mass. Other phosphorus sulfides may also be employed as diluents in the elemental pre-mix of phosphorus and sulfur such as the compounds $P_2S$ and $P_2S_3$. These compounds have low melting points and would aid in bringing the elemental sulfur and phosphorus into solution. A typical pre-mix for the production of phosphorus pentasulfide would comprise from about 72% to about 78% sulfur atoms, from about 25% to about 28% phosphorus atoms and from about 2% to about 10% by weight of the pre-mix phosphorus pentasulfide. Solid $P_2S_5$ added to the pre-mix of elemental phosphorus and sulfur allows the system, when crystallized, to be an air stable solid.

Other compatible diluents may also be employed to prepare the pre-mix of phosphorus and sulfur such as carbon disulfide but such diluent is usually removed by evaporation prior to reaching reaction conditions when bringing the mixture to the molten state. Such diluents are not preferred as they add a complication to the reaction involving the recovery of the diluent. It is preferred to employ as the diluent the product intended to be produced since it is not removed from the product thereby avoiding the expense of recovery and recycling.

When preparing a pre-mix of phosphorus and sulfur without a diluent as noted above, it has been found more convenient to add solid sulfur to molten phosphorus. Such addition is most conveniently performed by passing molten sulfur through a gaseous or liquid cooling phase in the mixing chamber so as to solidify the sulfur prior to its contact with the phosphorus layer. No reaction occurs and the sulfur dissolves in the molten phosphorus phase. Typical coolants which are employed for the purpose of reducing the temperature of sulfur and thus the mixing temperature are water or carbon dioxide gas. Such order of addition allows for more rapid and uniform mixing of the two molten materials. While combining the materials in the solid state followed by fusing the mixture is within the scope of this invention, such process is not preferred except in small scale operation. For large scale operation the blending of each material in the molten state is most convenient. In the preferred order of addition, indicated above, the most convenient and rapid means to achieve the desired result of uniform blending prior to allowing the process to proceed to reaction conditions is achieved. Further, the pre-mix, after thorough blending in the molten state, may be allowed to cool to the completely solid state and stored for future use. Upon reheating to the liquid state the pre-mix can be used in reactions involving phosphorus and sulfur.

In another embodiment of this invention, the cooling medium is replaced by a reactant in the reaction involving elemental sulfur and phosphorus. Sulfur is placed in the reactor and phosphorus is then fed to the reactor in a controlled manner. For example, rather than water or carbon dioxide in the mixing chamber as the coolant over molten elemental sulfur, a reactant such as an alcohol or mixture of alcohols can be employed in contact with the sulfur. Liquified phosphorus is fed to the system through the reactant layer. The phosphorus passes through the reactant layer (alcohol) reaching the liquid sulfur rich medium below the alcohol phase. Upon contact with the sulfur in the sulfur rich medium, which is held at activation temperature, it has been discovered that a reaction occurs involving not only the phosphorus and sulfur but also the reactant layer (alcohol) thereby producing a compound of the type known to be produced by the reaction of phosphorus pentasulfide and said reactant such as alcohol or alcohol mixture. The reaction may be controlled by the addition rate of the phosphorus so as to avoid excessive heating and other traditional problems involved with the reaction of phosphorus pentasulfide and organic materials such as alcohols. Secondarily, the rate of evolution of hydrogen sulfide is also more easily controlled by the process of this invention. Because of this discovery, there has been found a process for producing organic derivatives of phosphorus without the need for preparing, in a separate system, the well known intermediate, phosphorus pentasulfide.

The invention is more readily described by the attached figures.

DETAILED DESCRIPTION OF THE DRAWINGS

In FIG. 1 there is shown one possible manner of carrying out the process of this invention. The reactor in which the phosphorus and sulfur actually react is not shown as such reactors are well known in the art and can be operated substantially as presently practiced in accordance with this invention. In FIG. 1 there is shown a closed tank 1 equipped with a means 3 consisting of a shaft and impeller to agitate the lower portion of contents of the tank. The drive means for means 3 is not shown and may be any know phosphorus drive means. Into tank 1 is introduced molten sulfur through conduit 5. Typically the molten sulfur is maintained at about 150° C. to provide fluidity for handling purposes. The top portion 7 of tank 1 contains an atmosphere inert with respect to the molten sulfur such as carbon dioxide or nitrogen. Below the inert atmosphere of portion 7 is a layer of cooling medium 9, conveniently water or other cooling medium, through which the molten sulfur passes as indicated by particles 11. Cooling medium 9 is a liquid in which both sulfur and phosphorus are substantially insoluble. As the particles of molten sulfur pass through cooling medium 9 they are cooled but may remain in the amorphous state. Cooling medium 9 is held at a temperature in the range of from about 60° C. to about 70° C. and typically is 65° C. At a convenient point below portion 7 of the tank there is located conduit 13 which is provided to introduce phosphorus into tank 1. The phosphorus is also maintained in the liquid state. The sulfur and phosphorus combine in the tank in area 15 below the layer of cooling medium. By means of agitation, shown in FIG. 1 as a drive shaft and impeller 3, sulfur and phosphorus are thoroughly mixed prior to being discharged from the tank through conduit 17 by means of gravity of mechanical pumping (not shown). Conduit 17 is associated with a reactor wherein the sulfur and phosphorus are allowed to react at elevated temperatures, typically in the range of from about 120° C. to about 125° C. Typically, the reactor allows the phosphorus sulfide to be distilled out of the reactor by any suitable reactor known in the art to be employed for such reactions may be employed including those wherein the product of the reaction is removed as a liquid or solid.

While in the area 15 of the tank, phosphorus and sulfur are not only thoroughly mixed, but said mixture is also inspected to determine its constitution. Sampling means may be provided to examine the mixture optically or otherwise my be employed. Conduits associated with tank 1 may also be employed to withdraw, periodically or continuously, samples of the mixture for analysis. One such scheme of constant analysis is described in U.S. Pat. No. 5,260,026 to Feld et al. and such disclosure is hereby incorporated by reference. The present system is not recommended for use with laser spectroscopy as can be employed in the system described in the cited patent. Energy input into the present system is to be carefully controlled and limited to avoid the initiation of a reaction between the phosphorus and sulfur which, once initiated, would be self sustaining. In accordance with the results of the analysis of the mixture in area 15 of tank 1, the amount of sulfur or phosphorus may be varied to provide the precise ratio of the desired mixture. Typically, area 15 of tank 1 is sufficiently large so as to allow some amount of hold time in tank 1 such that adjustments of the feed rates of phosphorus or sulfur can be carried out. Another advantage of the process of this invention is the fact that the size of tank 1 is minimized so as to provide a small amount of inventory of phosphorus and sulfur pre-mix. Since the materials being handled are in the liquid state the process is easily conducted with pumps at controlled rates and with mixtures which do not react until placed into a suitable reactor which also may be of minimal size.

Figure 2:
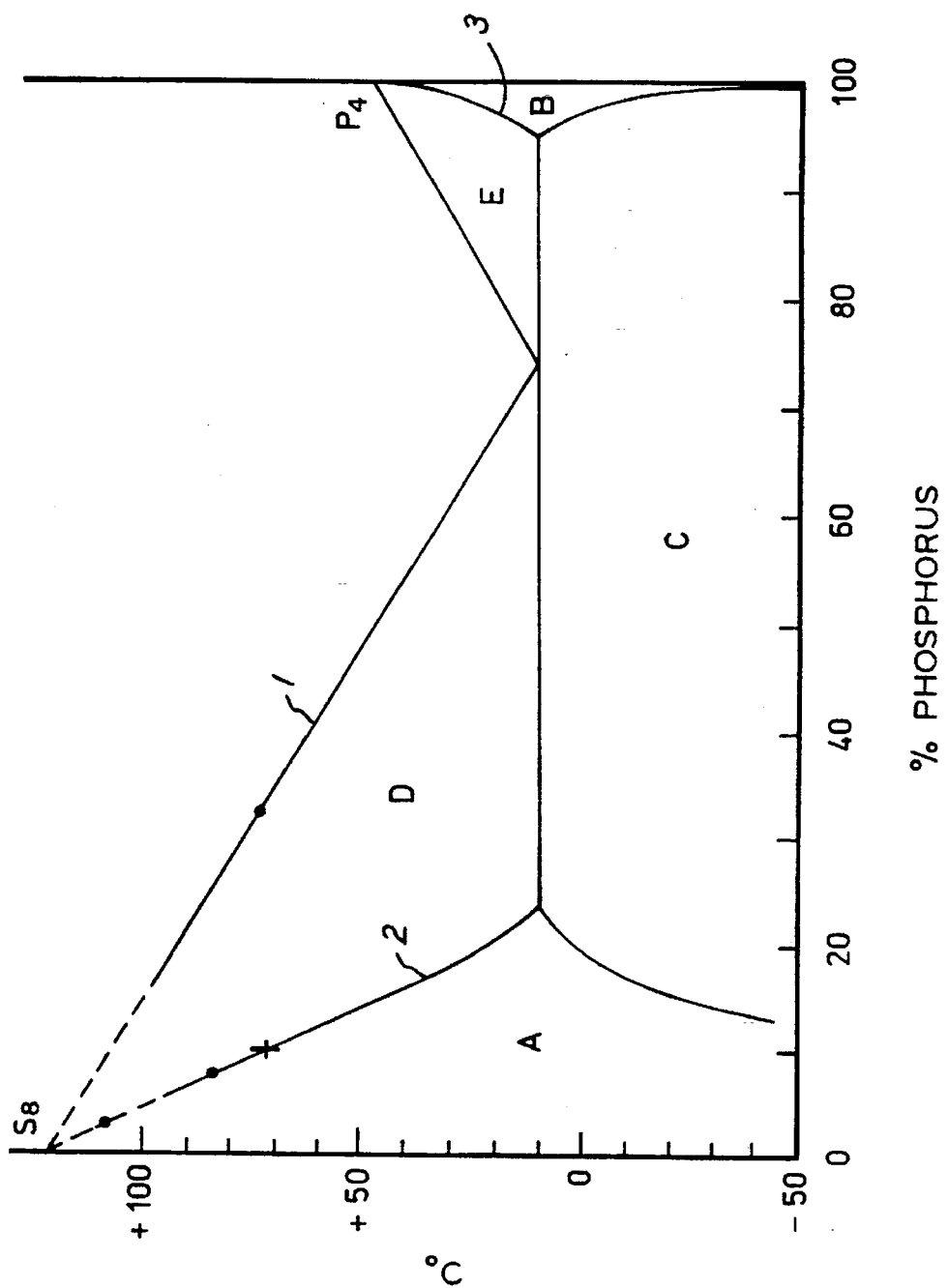
FIG. 2 is a phase diagram of the solid-liquid relationship of white phosphorus/sulfur elemental mixtures at temperatures below about 100° C.

In FIG. 2 there is shown a phase diagram indicating mixtures of white phosphorus and sulfur at temperatures below about 100° C. In FIG. 2, the abscissa indicates the amount in percent of phosphorus (atoms) in the mixture. The ordinate indicates the temperature in degrees C. Line 1 in FIG. 2 defines the lowest temperature of totally liquid (molten) mixtures. As can be seen in FIG. 2, a eutectic mixture occurs at 74 atom-percent phosphorus having a liquidus temperature of 9.8° C. In area A of FIG. 2 there occurs solid solutions having the same crystal structure of the $S_8$ molecule. In area B of FIG. 2, there occurs solid solutions wherein the crystal structure is the same as the $P_4$ molecule. In area C of FIG. 2, there occurs solid solutions which are mixtures of crystals of both the A and B types. In area D of FIG. 2, varying amounts of crystals of the A type are found in a liquid medium with the amounts of crystalline material dependent on temperature as shown by line 2. In area E of FIG. 2 there occurs crystals of the B type in liquid wherein the amount of crystals is dependent upon temperature as indicated by line 3.

In the improved processes of this invention, all of the mixtures shown in FIG. 2 are useful. The liquid mixtures in areas D and E of FIG. 2 are easily handled whereas those mixtures in areas A, B and C are solid. However, the reactions in which the phosphorus and sulfur take part are normally conducted at temperatures which would render all of the mixtures described in FIG. 2 liquid or mostly liquid.

Figure 3:
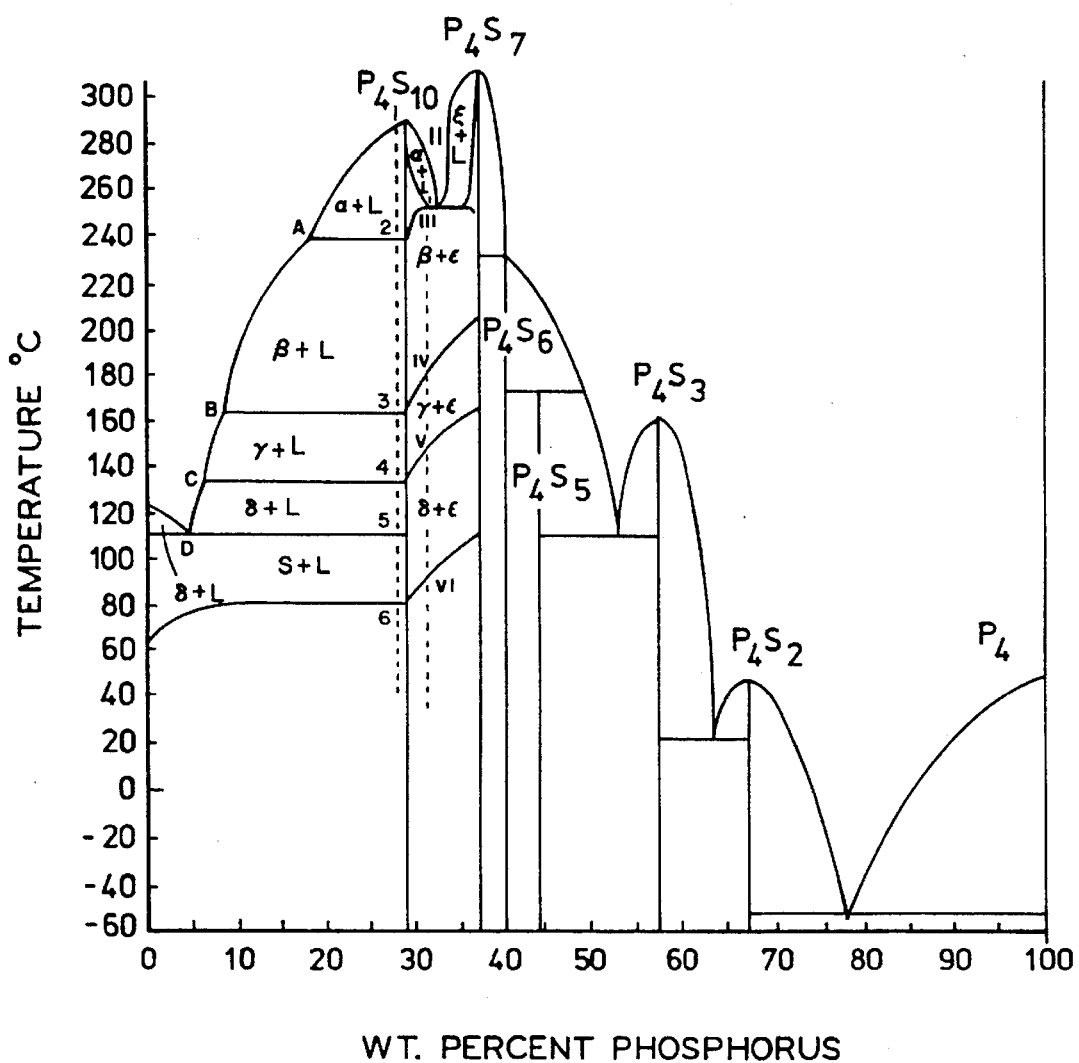
FIG. 3 is a phase diagram of compounds produced in the reaction of phosphorus with sulfur above the activation temperature.

In FIG. 3 there is shown the phase states of the reaction products of phosphorus and sulfur. The liquid/solid phases of such compositions are seen to vary according to the amount of phosphorus in the system with polymorphs evident in the sulfur-rich side of the system. In part, FIG. 3 is taken from the diagram of R. Forthmann and A. Schneider, Z. Physik. Chem. (49) p. 22, 1966 with added information relating to the sulfur rich compositions having less than the amount of phosphorus required for phosphorus pentasulfide. A composition having 79% phosphorus is shown to be a liquid which does not solidify until it reaches temperatures more that 50° C. below 0° C.

THIONATION REACTIONS

As will be shown below by the various working examples of this invention, the process of this invention provides a wide range of thionation reactions. Previously such reactions employed an organic thionation reagent such as an aryl thionophosphine sulfide, typically 2,4-bis(p-methoxyphenyl)-1,3-dithiadiphophetane-2,4,-disulfide, also known as "Lawessen's Reagent". The thionation reagent was prepared by the reaction of an aryl compound such as anisole and phosphorus pentasulfide. A thorough discussion of this reagent and variations thereof as well as its various uses is provided in a article appearing in Tetrahedron, Vol. 41, No. 22 pp. 5061–5087 (1985) by M. P. Cava and M. I Levinson, which is incorporated herein by reference.

It has now been discovered, in accordance with this invention, that elemental phosphorus and elemental sulfur can be employed directly to prepare such useful compounds as petroleum additives, rubber chemicals, synthesis intermediates and insecticides by direct reaction with the appropriate organic material, elemental sulfur and elemental phosphorus in the presence of a Lawessen's Reagent organic precursor without the need to form separately the previously known intermediate, Lawessen's Reagent.

In accordance with the process of this invention there is avoided the need not only for the preparation of phosphorus pentasulfide but also the avoidance of the need for an intermediate prepared by the reaction of an Lawessen's organic precursor and phosphorus pentasulfide to provide Lawessen's Reagent.

In general, the process of this invention involves the reaction of elemental phosphorus and elemental sulfur in amounts generally corresponding to $P_2S_5$ which, as noted above, is usually, by weight, in the range of from about 72% to about 75% sulfur atoms and from about 25% to about 28% phosphorus atoms with an organic compound to be thiohated in the presence of an organic precursor of a Lawessen's Reagent. The reaction mixture typically comprises elemental sulfur, an organic compound to be thanatoid and a Lawessen's Reagent organic precursor. This reaction mixture is usually heated under an inert atmosphere and then elemental phosphorus is introduced into the reaction mixture. The reaction mixture is raised to a degree sufficient to cause the elemental phosphorus and elemental sulfur to react. Typically the reaction temperature is from about 115° C. to about 125° C. Once the reaction is initiated, the temperature is usually controlled by the rate of addition of phosphorus. Combining an organic precursor reactant typically employed to prepare a Lawessen's Reagent under conditions allowing for the reaction of the elemental phosphorus and elemental sulfur and an organic reactant to be thionated provides a thionated organic product.

Typical organic materials are disclosed in the publication noted above as organic precursor reactants to form various Lawessen's Reagents by reaction with phosphorus pentasulfide. Such aromatic materials include anisole, naphthalene, methoxy benzene, ethoxy benzene, toluene, naphthalene, etc. Reactions previously involving Lawessen's Reagent for thionation can now be performed in accordance with this invention by employing the above noted organic precursor reactant for Lawessen's Reagent, elemental phosphorus, elemental sulfur and the organic material to be thanatoid.

Any number of organic compounds can be thanatoid in accordance with this invention including aromatic and aliphatic ketones which are converted to the corresponding thioketones. Other organic compounds include Grignard reagents, amines, alkoxides and hydrazones which, in the process of this invention, yield dithiophosphinic acids, dithiophosphonoamides, dithiophosphonates and diazaphospholines, respectively. Also, O- and S-substituted esters and lactones are converted to the corresponding thioester, dithioesters and thiones by employing the Lawesson's Reagent organic precursor reactant, elemental phosphorus, elemental sulfur and the organic material to be thanatoid.

Aryl, alkyl and unsaturated amides and lactams can be transformed into their corresponding thio-analogs by the process of this invention where the Lawesson's Reagent organic precursor, elemental phosphorus, elemental sulfur and the organic material to be transformed are employed. Many examples of thiocarboxamides are listed in the above noted publication by M. P. Cava and M. I. Levinson which can now be prepared by the process of this invention, bypassing the preparation and use of phosphorus pentasulfide or Lawessen's Reagent. Hydroxy substituted thiobenzamides can be prepared from hydroxy benzamides and a Lawessen's Reagent organic precursor, elemental phosphorus and elemental sulfur. In a similar manner substituted and unsubstituted β-thiolactams are prepared from β-lactams; enaminothiones are prepared from enaminones; thiohydrazides from hydrazides; hydroxypyidazines and hydroxypyridazones to mercaptopyridazines and mercaptopyridazones; ureas to thioureas; and thionations of amides giving thioamides.

Virtually any reaction in which a Lawessen's Reagent is employed with an organic compound for thionation can now be replaced by the process of this invention wherein elemental phosphorus, elemental sulfur, an organic precursor for Lawessen's Reagent and an organic compound to be thionated are caused to react.

Pesticides can be synthesized conveniently in accordance with this invention by the reaction of aryl or alkyl alcohols with elemental phosphorus and elemental sulfur to yield dialkyl phosphorodithioc acids. In most instances the alcohol is placed in a suitable reactor together with elemental sulfur and as elemental phosphorus is added to the reactor. Upon heating the reactor contents to an activation temperature whereby the elemental sulfur and elemental phosphorus react, the phosphorodithioate is formed in accordance with the type of alcohol employed. A suitable reactor is usually equipped with a reflux condenser, means to provide an inert atmosphere and heating means. Most alcohols are high boiling, that is, above the activation temperature of the elemental phosphorus and elemental sulfur. In such instances the reaction occurs directly and efficiently upon reaching the sulfur/phosphorus activation temperature. However, in the case of lower boiling alcohols, such as methyl, ethyl, and propyl alcohols, including isomers thereof, the initial reaction temperature is maintained slightly below the boiling point of the alcohol. While initially the reaction rate at lower temperatures is relatively slow, as the production of the dialkyl phosphorodithioic acids or esters proceeds, the boiling point of the reaction mixture increases allowing for an increase in reaction temperature thereby increasing the reaction rate. It is preferred to employ the pre-mix of phosphorus and sulfur described above with low boiling alcohols rather than the independent addition of each element to the reactor. Typically, alkyl alcohols having from 1 to 20 carbon atoms are commonly available and useful in the process of this invention. However any alcohol which can be rendered liquid at reaction temperatures of from 80° to 350° C. may be conveniently employed in the processes of this invention.

Thionation of of aryl and alkyl acids can also be carried out in accordance with this invention in similar manner as described above with respect to alcohol. It has been found that elemental phosphorus and elemental sulfur in a ratio generally corresponding to $P_2S_5$. Thioacids result from the process. Commonly available acids include benzoic acid, alkyl acids wherein the alkyl group contains from 1 to 20 carbon atoms, polynuclear aryl acid include naphthoic acid, also included are aryl substituted alkyl acids such as substituted of unsubstituted phenoxyacetic acids.

NOKES REAGENT

There has been disclosed in U.S. Pat. No. 2,811,255 a processing aid for recovery of metals from ore, said patent is hereby incorporated by reference. The processing aid is described therein as both a depressant reagent as well as a detergent reagent which reduces frothing as well as improving metal recovery. According to the patent, the processing aid is sodium thiophosphate which is prepared by dissolving sodium hydroxide in water followed by the addition of phosphorus pentasulfide. This mixture is agitated until the sulfide is completely dissolved. Typically, cooling means is provided to keep the temperature of the mixture below the boiling point. Hydrogen sulfide is released as the thiophosphate forms. This very successful reagent takes its name from the inventor in the above noted U.S. patent.

In accordance with this invention Nokes Reagent is prepared by introducing sulfur into an aqueous caustic solution and then introducing phosphorus into the sulfur layer with sufficient heating to initiate a reaction of the phosphorus and sulfur. Contact with the aqueous caustic solution is avoided by piping the phosphorus through into the sulfur layer where it reacts at the activation temperature. The addition of phosphorus is controlled so as to control the rate of reaction and the resultant reaction temperature as the Nokes Reagent forms. The procedure of this invention thus avoids the necessity of preparing phosphorus pentasulfide, its shipping, storage and handling.

ALTERNATIVE PROCESSES

Because of the wide variety of organic and inorganic compounds which can be employed in the process of this invention various modes of addition must be employed. The above processes can be operated in various ways and embodiments in accordance with this invention as the reactivity/physical properties of various reactants with respect to phosphorus and sulfur is well known. That is, either sulfur or phosphorus can be added to a suitable reactor in any order or together in a pre-mix as noted above with respect to the process for preparing phosphorus sulfides. Such modifications include reversing the addition, that is, adding sulfur to a suitable reactor containing phosphorus and the other reactants.

The above disclosure generally describes the invention. A more complete understanding can be obtained by reference to the following specific examples which are provided herein for the purposes of illustration only and are not to limit the scope of the invention.

DESCRIPTION OF THE PREFERRED EMBODIMENTS

EXAMPLE 1

Into a flask equipped with two side arms and a heating mantle was place 0.2782 g of sulfur, 0.1075 g of phosphorus and 0.154 g of phosphorus pentasulfide while the flask was swept with nitrogen. A thermocouple was placed into the flask to monitor the temperature of the contents. With the flask covered and with continuous nitrogen purge the flask was heated thereby fusing the contents into a homogeneous solution. This solution was then heated to 124° C. whereupon an exothermic reaction occurred raising the temperature to 225° C. After cooling the product was analyzed by x-ray diffraction indicating that $P_2S_5$ was produced in the reaction.

EXAMPLE 2

To a flask equipped as described in Example 1 there was placed 0.112 g of phosphorus and 0.3153 g of sulfur which is the correct proportions for $P_2S_5$. With a constant nitrogen purge and the flask covered, the contents was heated to at temperature of 77.5° C. which resulted in the formation of a completely liquid mixture in the flask. This mixture was then heated to a temperature in the range of from about 119° C. to about 122° C. resulting in an exothermic reaction. The heating means was turned off and the reaction raised the temperature of contents to 520° C. Phosphorus pentasulfide was produced.

EXAMPLE 3

Into a flask equipped as described in Example 1 was added 0.1210 g of phosphorus, 0.3147 g of sulfur and 0.0285 g of $P_2S_5$. The contents were heated slowly to place the materials into a fused mixture. The mixture appeared to fuse at. After thoroughly mixing the fused mass the temperature was raised to the range of 117° C. to about 122° C. which initiated an exothermic reaction. The heating was discontinued and the contents of the flask reached a temperature of 248° C. Phosphorus pentasulfide was produced.

EXAMPLE 4

A series of experiments were conducted to determine the safety of the pre-mix of elemental phosphorus and sulfur. The mixtures contained the ratio of phosphorus and sulfur corresponding to phosphorus pentasulfide. To these mixtures was added various amounts of the preformed compound phosphorus pentasulfide. After thorough mixing in the molten state the mixtures were cooled to room temperature thereby solidifying them. The mixtures were then exposed to the air at room temperature (approximately 22° C.). The results of these experiments appear in Table I below. In Table I the amount of $P_2S_5$ is provided in percent by weight of the total sample.

TABLE I

| Sample | wt % $P_2S_5$ Added | Comments on Pyrophosphoric Nature |
| --- | --- | --- |
| Control | None | Spontaneous burning at room temperature |
| 1 | 4.0 | No burning at room temp. |
| 2 | 4.0 | No burning at room temp. |
| 3 | 4.0 | No burning at room temp. |
| 4 | 2.0 | No burning at room temp. |
| 5 | 6.0 | No burning at room temp. |
| 6 | 8.5 | No burning at room temp. |

From the data in the above Table I, it has been shown that pre-mix compositions of this invention containing $P_2S_5$ at dopant levels are non-pyrophoric at room temperature. The usefulness of the pre-mix feed material provided in accordance with this invention is enhanced by pacification of an otherwise pyrophoric material.

EXAMPLE 5

A series of experiments was conducted to demonstrate the reduced exotherm occurring in the reaction of phosphorus and sulfur in the process for producing phosphorus pentasulfide. Mixtures of phosphorus and sulfur were prepared and mixed with varying amounts of $P_2S_5$. After thorough mixing in the molten state the mixtures were allowed to react to produce phosphorus pentasulfide in a round bottom flask equipped with a temperature sensing means and a heating mantle. The initiation temperature and maximum exotherm temperature of the adiabatic reaction was observed. Notes were also taken indicating the character of the reaction. The data and observations are summarized below in Table II wherein the amount of $P_2S_5$ is given in weight percent of the total mixture and the temperature is provided in degree C.

TABLE II

| Sample | wt % $P_2S_5$ | Initial Temp. | Exotherm Temp. | Comments |
| --- | --- | --- | --- | --- |
| control | no | 119 | 520 | explosion & fire |
| control | no | 121 | 580 | explosion & fire |
| 1 | 4.0 | 124 | 225 | no explosion or fire; flashing |
| 2 | 6.25 | 120 | 236 | no explosion or fire; flashing |
| 3 | 6.50 | 122 | 248 | no explosion or fire; flashing |

From the data in Table II it is shown that the exotherm temperature (the highest temperature observed during adiabatic reaction) of the reaction producing $P_2S_5$ is reduced to about one-half that of the un-doped mixtures and that the reaction took place with explosion and fire. From the above it is seen that processes involving the reaction of phosphorus and sulfur in the molten state can be carried out at lower temperatures and with greater safety then previously known.

EXAMPLE 6

The pre-mix of this invention was employed in a reaction involving phosphorus and sulfur in the molten state wherein a dialkyl phosphorodithioic acid was produced directly by the incorporation into the molten mixture of elemental phosphorus and elemental sulfur an appropriate amount of an alcohol. Into a 10 ml flask is placed 2.4023 g of Oxo alcohol (a mixture containing $C_7$ and $C_9$ alkyl alcohols. The alcohol mixture was boiled without a reflux condenser at 105° C.–110° C. for 2–4 minutes under nitrogen to remove water and low boiling impurities. After the purification step, only 2.3791 g of alcohol remained. The purified alcohol was cooled to 40° C. and combined with 0.7303 g of reagent grade sulfur. This mixture was stirred under reflux and an atmosphere of nitrogen for 5 minutes at a temperature under 30° C. Then, 0.2841 g of dry white phosphorus was transferred into the mixture of sulfur and alcohol and thoroughly mixed under a nitrogen atmosphere for 15 minutes. The stirred mixture was slowly heated to a temperature of 107°–114° C. for two hours and then the temperature was raised to the range of 115°–122° C. to increase reaction rate and insure the complete reaction of the phosphorus/sulfur mixture. As the reaction proceeded hydrogen sulfide was release and removed overhead. The reaction was completed in about 5 hours. In this reaction it was found to be critical to the control of the reaction to maintain the temperature under 114° C. during the first 2 hours. Higher temperatures during this time resulted in an exothermic reaction which is very difficult to control. The product, a liquid containing small amount of silver white/yellow crystals at room temperature was analyzed by $^{31}P$ NMR which indicated that it contained 89%, by weight, pure dialkyl phosphorodithioic acid. Such result is surprising because the known prior art reaction of said alcohols with preformed $P_2S_5$ results in an average production of about 80% desired product. A series of reactions was performed as described above with varying amounts of excess alcohol and slight adjustment of the phosphorus content of the pre-mix composition. The pre-mix of elemental phosphorus and elemental sulfur generally corresponded to phosphorus pentasulfide. In Table III below percent yield is based upon the amount of desired product in the final reaction mixture. In Table III the result of a typical commercial production run is shown in which the alcohol is reacted under typical prior art conditions with preformed phosphorus pentasulfide.

TABLE III

| Sample | % $P_4$ | % Excess Alcohol | % Yield |
| --- | --- | --- | --- |
| commercial | — | 18* | 78.18 |
| 1 | 27.85 | 2.7* | 87.91 |
| 2 | 27.85 | 4.0* | 89.40 |
| 3 | 27.85 | 4.0* | 86.18 |
| 4 | 28.00 | 6.50 | 76.45 |
| 5 | 28.00 | none | 88.73 |
| 6 | 28.00 | none | 81.08 |

*Amount is approximate

From the above data it is seen that a small excess of alcohol above the stoichiometric amount provides the highest yield of desired product.

EXAMPLE 7

The procedure of Example 6 was repeated except that a series of different alcohols was employed. In all runs the amount of phosphorus was 27.80% on the basis of the total amount of elemental phosphorus and elemental sulfur. The amount of excess alcohol over or below the stoichiometric amount in each run is shown in Table IV below. The yield shown in Table IV is based upon theoretical yield of the dialkyl phosphorodithioic acid produced.

TABLE IV

| Run No. | Alcohol | Excess % Alcohol | % Yield |
| --- | --- | --- | --- |
| 1 | n-butanol | 2.10 | 82.87 |
| 2 | 2-ethyl-1-hexanol | 2.20 | 97.50 |
| 3 | n-pentanol | 3.20 | 82.51 |
| 4 | n-pentanol | 2.30 | 82.66 |
| 5 | iso-octanol | 2.60 | 93.54 |
| 6 | n-pentanol | 2.80 | 81.37 |
| 7 | n-pentanol | −1.20 | 78.60 |
| 8 | 40/60 ww % n-pentanol & iso-butanol | 2.20 | 88.14 |
| 9 | n-butanol | 2.50 | 79.84 |
| 10 | n-hexanol | 2.30 | 80.00 |
| 11 | 20/40/40 ww % iso-propanol/iso-butanol/2-ethyl-1-hexanol | 4.80 | 98.40 |

EXAMPLE 8

Into a 50 ml round bottom flask there was placed a stirring bar, 12.5 g reagent grade toluene, 5.37 g of anisole (a Lawessen's Reagent organic precursor), 3.57 g of 3,2 pyridazone and 3.38 g of sulfur. The flask was fitted with a reflux condenser and then the mixture was stirred under a blanket of inert nitrogen for 10 minutes. Then, 1.2810 g of phosphorus was added to the flask with vigorous stirring for another 15 minutes under inert atmosphere at room temperature. The addition of phosphorus is controlled thereby acting as a control for the reaction. With continued mixing under reflux and with inert atmosphere, the temperature of the contents of the flask was raised to the range of from 115°–127° C. for 7 hours. There resulted the formation of dark emerald green crystals of 3-mercaptopyridazine which was recovered from the reaction mixture by filtration.

EXAMPLE 9

The procedure of Example 8 was repeated with the exception that an equivalent amount of 3,6- dihydroxypyridazine was substituted for the 3,2-pyridazone. The reaction resulted in the production of dark orange crystals of 3,6-dimercaptopyridazine.

EXAMPLE 10

Into a 25 ml round bottom flask was placed 6.57 g of m-cresol which was heated to a temperature in the range of from 104° C. to bout 108° C. to remove water. The remaining m-cresol weighed 6.42 g. The m-cresol was added 2.35 g of sulfur at a pot temperature of below 37° C. The mixture was stirred under inert nitrogen atmosphere and the flask was fitted with a reflux condenser while the temperature was held below 30° C. Then 0.91 g of white phosphorus was added quickly to the flask after which the system was purged to assure an inert atmosphere. The temperature was then increased to about 104°–105° C. and held for about 5 hrs. The heating was interrupted over night and resumed at a range of 110°–120° C. for an additional 1 hr. and 45 minutes. A reaction occurred as indicated by the evolution of hydrogen sulfide and the elimination of phosphorus and sulfur from the flask. It appeared that a diaryl phosphorodithioic acid was produced.

EXAMPLE 11

Into a 25 ml flask was placed 10.3 g of p-nonylphenol. The material was heated under an inert nitrogen atmosphere with stirring at a temperature in the range of 105°–110° C. for 15 minutes to remove moisture thereby reducing the weight of the alkyl phenol to about 10.2 g. After cooling the alkyl phenol below 37° C., 1.82 g of sulfur was added to the flask with stirring. A reflux condenser was fitted to the flask and the mixture was heated under a nitrogen atmosphere to a temperature below 32° C. Then, 0.7 g of phosphorus was added to the flask and an inert atmosphere was restored. The flask was allowed to cool to room temperature. Heat was applied to the flask and the temperature raised to 113°–115° C. for about 1 hr. Hydrogen sulfide began to evolve from the flask as the temperature was increased above about 99.8° C. and increased in amount as the temperature increased. The temperature was then increased to the range of 118°–123° C. for 2 hrs. After a shut down overnight, the system was reheated to the range 118–125 for an additional 1 hr. 40 minutes. The phosphorus and sulfur were no longer visible and it appeared that a diaryl phosphorodithioic acid was made.

EXAMPLE 12

Into a 25 ml round bottom flask was placed 6.94 g of hexanoic acid. The acid was heated to a boil to remove water and then cooled to below 35° C. leaving 6.8 g of hexanoic acid left in the flask. There was quickly added 1.86 g of sulfur to the flask followed by stirring under a nitrogen atmosphere for a period of from 10 to 15 minutes. Then 0.72 g of white phosphorus was added and the mixture heated under nitrogen with stirring. The temperature was raised to 101°–103° C. for one hr. as hydrogen sulfide began to evolve and then to 104°–110° C. for an additional 7 hrs. at which time all of the phosphorus and sulfur appeared to react. There appeared to be produced a thiocarboxylic acid.

EXAMPLE 13

Into a reactor equipped with a reflux condenser, heating mantle, stirring means and means to supply an inert nitrogen atmosphere there is charged 3.5488 g of isopropyl alcohol and 2.2360 g of sulfur. This mixture is stirred for 15 minutes under an inert atmosphere and reflux conditions. Then, 0.8780 g of phosphorus was quickly introduced into the mixture with continued stirring. The temperature of the mixture upon addition of the phosphorus was about 73° C. and was gradually raised over a 2 hrs. period to 76° C. Hydrogen sulfide began to evolve from the reactor as the temperature increased over about 73° C. and increased in volume as the temperature was increased. After 2 hrs., the temperature was increased slowly over 80° C. for 1.5 hrs. to 82° C. Then, as the amount of desired product increased in the reaction mixture, the temperature was increased to 86° C. and held at that temperature for an additional 11 hrs. All of the phosphorus and sulfur had disappeared and the temperature of the reactor increased to the range of 130°–132° C. Analysis by proton NMR of the reaction mixture indicated a yield of 85% of theoretical based upon the amount of alcohol employed.

EXAMPLE 14

The procedure of Example 13 was repeated except that ethanol replaced isopropanol. A 7% excess of ethanol totaling 3.8990 g was employed and a pre-mix of phosphorus and sulfur was added to the reactor. The premix totaled 3.3712 g, comprised of 0.9355 g of phosphorus and 2.4357 g of sulfur. After preheating the alcohol under inert atmosphere for 15 minutes in the reactor the pre-mix was added at ambient room temperature. The reaction mixture was heated slowly with the following profile:

| Temperature Range - °C. | Time - hrs. |
|---|---|
| 78–81.5 | 5 |
| 82–87 | 3 |
| 90–105 | 2 |
| 102–130 | 1 |

The pre-mix disappeared from the reactor after about 10 hrs. reaction time after which the temperature rose quickly during the last hour. Analysis of the reaction mixture indicated contained dimethyl phosphorodithioate triester in a 60% yield of theoretical based upon the amount of phosphorus employed.

Although the invention has been described in terms of specific embodiments which are set forth in considerable detail, it should be understood that this description is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A process for preparing a dialkyl phosphorodithioic acid comprising
   (a) combining an alkyl alcohol with elemental sulfur and white phosphorus, wherein said sulfur and phosphorus are premixed at a temperature below the activation temperature of sulfur and phosphorus and are present in a ratio of two moles of phosphorus to five moles of sulfur;
   (b) heating the mixture of (a) to a temperature to cause the sulfur and phosphorus to react; and
   (c) recovering a dialkyl phosphorodithioic acid from the reaction mixture.

2. The process of claim 1 wherein the mixture of step (a) contains a stoichiometric excess of alkyl alcohol.

3. The process of claim 2 wherein the alcohol is a mixture of $C_7$–$C_9$ alkyl alcohols.

4. A process for the production of dialkyl phosphorodithioic acid comprising providing a reactor containing a bottom layer of elemental sulfur under and in contact with a layer of liquid, high boiling alkyl alcohol, admitting elemental phosphorus into the reactor and passing through the layer of alkyl alcohol whereby it contacts the layer of sulfur at a reaction temperature of sulfur and phosphorus whereby there occurs a reaction between the phosphorus, sulfur and alcohol producing said dialkyl phosphorodithioic acid.

5. The process of claim 4 wherein the alcohol is selected from the group consisting of n-butanol, 2-ethyl-1-hexanol, n-pentanol, and iso-octanol.

6. A process for the production of a dialkyl dithiophosphorodithioate which comprises mixing an alcohol selected from the group consisting of methanol and ethanol with white phosphorus and elemental sulfur, wherein the said phosphorus and sulfur are present in a molar ratio of 2:5, wherein a premix of said phosphorus and sulfur is added to the alcohol in a suitable reactor and the temperature is raised to the activation temperature for a reaction of said phosphorous and sulfur.

7. A process for preparing diaryl phosphorodithioic acid which comprises combining in a suitable reactor a substantially anhydrous hydroxy substituted aryl compound and a mixture of elemental sulfur and white phosphorus while heating the reactor contents to a temperature whereby said phosphorus and sulfur react the molar ratio of phosphorus and sulfur corresponding to 2:5.

8. The process of claim 4 wherein the aryl compound is m-cresol.

9. The process of claim 1 wherein the aryl compound in p-nonyl phenol.

* * * * *

UNITED STATES PATENT AND TRADEMARK OFFICE
CERTIFICATE OF CORRECTION

PATENT NO.:   5,663,402

DATED:        September 2, 1997

INVENTORS:    Edward J. Griffith and Toan M. Ngo

It is certified that error appears in the above-identified patent and that said Letters Patent is hereby corrected as shown below:

```
Cover page, item [73] Assignee: Monsanto Company, St.
Louis, Missouri
```

Signed and Sealed this

Seventh Day of July, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.   :  5,663,402

DATED        :  September 2, 1997

INVENTOR(S)  :  Edward J. Griffith, et al.

It is certified that error appears in the above-identified patent and that said Letters Patent are hereby corrected as shown below:

Column 3, line 24, "allottopic" should read --allotropic--.
Column 7, line 27, "thiohated" should read --thionated--.

Signed and Sealed this

Twenty-second Day of May, 2001

Attest:

NICHOLAS P. GODICI

Attesting Officer        Acting Director of the United States Patent and Trademark Office